(12) United States Patent
Jans et al.

(10) Patent No.: US 9,921,163 B2
(45) Date of Patent: Mar. 20, 2018

(54) METHOD AND DEVICE FOR DETECTING ANALYTES

(71) Applicants: IMEC VZW, Leuven (BE); Panasonic Corporation, Osaka (JP)

(72) Inventors: Hilde Jans, Leuven (BE); Masahiko Shioi, Osaka (JP); Karolien Jans, Hasselt (BE); Liesbet Lagae, Leuven (BE)

(73) Assignees: IMEC vzw, Leuven (BE); Panasonic Corporation, Osaka (JP)

(*) Notice: Subject to any disclaimer, the term of this patent is extended or adjusted under 35 U.S.C. 154(b) by 377 days.

(21) Appl. No.: 14/180,100

(22) Filed: Feb. 13, 2014

(65) Prior Publication Data

US 2014/0234219 A1    Aug. 21, 2014

Related U.S. Application Data

(60) Provisional application No. 61/765,367, filed on Feb. 15, 2013.

(51) Int. Cl.
 - *A61K 49/00* (2006.01)
 - *G01N 21/65* (2006.01)
 - *G01N 21/64* (2006.01)

(52) U.S. Cl.
 CPC ......... *G01N 21/658* (2013.01); *G01N 21/648* (2013.01); *A61K 49/0004* (2013.01)

(58) Field of Classification Search
 USPC .......................................................... 424/9.1
 See application file for complete search history.

(56) References Cited

U.S. PATENT DOCUMENTS

| | | |
|---|---|---|
| 6,750,311 B1 | 6/2004 | Van Antwerp et al. |
| 2002/0026108 A1 | 2/2002 | Colvin, Jr. |
| 2003/0059820 A1* | 3/2003 | Vo-Dinh .............. B01J 19/0046 506/3 |
| 2009/0014340 A1 | 1/2009 | Williams et al. |
| 2009/0203980 A1 | 8/2009 | Carlson et al. |
| 2009/0251693 A1 | 10/2009 | Hu |
| 2013/0035567 A1* | 2/2013 | Strano ................ A61B 5/14532 600/316 |

FOREIGN PATENT DOCUMENTS

| | | |
|---|---|---|
| EP | 2 161 575 A2 | 3/2010 |
| WO | 2011/053247 A1 | 5/2011 |

OTHER PUBLICATIONS

Auchinvole et al. (ACSnano, 2012, 6, 888-896).*
Kitano (Makromol. Chem., Rapid Commun. 1991, 12, 227-233).*
Rogers, Kim R., "Principles of Affinity-Based Biosensors", Molecular Biotechnology, vol. 14, 2000, pp. 109-129.
Boduroglu, Serhan, "New Supramolecular Approach for Sugar Analysis", Dissertation Presented to The Graduate Faculty of the University of Akron, Dec. 2006, pp. 1-138.
Yonzon, Chanda Ranjit et al., "A Glucose Biosensor Based on Surface-Enhanced Raman Scattering: Improved Partition Layer, Temporal Stability, Reversibility, and Resistance to Serum Protein Interference", Analytical Chemistry, vol. 76, No. 1, Jan. 1, 2004, pp. 78-85.
Stuart, Douglas A. et al., "Glucose Sensing Using Near-Infrared Surface-Enhanced Raman Spectroscopy: Gold Surfaces, 10-Day Stability, and Improved Accuracy", Analytical Chemistry, vol. 77, No. 13, Jul. 1, 2005, pp. 4013-4019.
Yuen, Jonathan M. et al., "Transcutaneous Glucose Sensing by Surface-Enhanced Spatially Offset Raman Spectroscopy in a Rat Model", NIH Public Access, Author Manuscript, Published in Final Edited Form as: Anal Chem., vol. 82, No. 20, Oct. 15, 2010, pp. 1-9.
Culha, Mustafa et al., "Surface-Enhanced Raman Scattering as an Emerging Characterization and Detection Technique", Hindawi Publishing Corporation, Journal of Nanotechnology, vol. 2012, Article ID 971380, 2012, 15 pages.
Stuart, Douglas A. et al., "Glucose Sensing Using Near-Infrared Surface-Enhanced Raman Spectroscopy: Gold Surfaces, 10-Day Stability, and Improved Accuracy", Analytical Chemistry, May 10, 2005, 7 pages.

* cited by examiner

*Primary Examiner* — Michael G Hartley
*Assistant Examiner* — Melissa J Perreira
(74) *Attorney, Agent, or Firm* — McDonnell Boehnen Hulbert & Berghoff LLP

(57) ABSTRACT

A method (200) for determining a concentration of an analyte in a fluid or fluid sample, comprises: providing (201) a SERS substrate comprising receptor molecules (107) capable of binding competitor molecules (106); contacting (202) the SERS substrate (102) with a fluid (sample) comprising analyte (108) and such competitor molecules (106); radiating (203) the SERS substrate (102) with a light source while measuring a SERS signal; and determining (205) a concentration of the analyte (108) based on the measured signal level.

A corresponding device and system are also provided.

18 Claims, 10 Drawing Sheets

3TBA

PBA

4FFPBA*

3APBA

5FMPBA*

METHOD AND DEVICE FOR DETECTING ANALYTES

FIELD OF THE INVENTION

The present invention relates to biosensors, more specifically to surface enhanced Raman biosensors. In particular the invention relates to a method, a device, a system and a use for indirectly determining the concentration of an analyte in a fluid or fluid sample.

BACKGROUND OF THE INVENTION

Diabetes affects millions of people worldwide and this number is only increasing making it a recognized global health problem. The chronic disease results in long-term health disorders mainly including cardiovascular diseases and blindness. Currently, there is still no cure for diabetes available. Together with a healthy lifestyle, maintaining a normal blood glucose concentration by making therapeutic interventions (i.e. insulin delivery) is crucial for the prevention of the associated complications. Hereto glucose monitoring technologies are being used. By carefully controlling the blood glucose concentration, the quality and length of life will clearly improve.

Nowadays, most diabetes patients rely on hand-held glucose meters that record glucose levels in blood drawn via finger pricking. Since this procedure is not pain free and does not allow easy monitoring during the patient's sleep, researchers are looking into 'user-independent continuous glucose monitors' that can be implanted or used transdermal, i.e. through the human skin. Transdermal monitors in contact with the skin are categorized as non-invasive, but suffer from slow penetration and as a result a time lag between the blood-glucose level and the measured glucose level penetrating the skin (e.g. skin blister). Moreover these types of sensors can generate false signals when interacting with other molecules present in the sampled fluid and they are prone to environmental factors like e.g. temperature.

On the other hand, fully implantable devices are categorized as more invasive, but hold great promise since they increase the comfort and ease of adaptability for the patient if they can operate for a long time. In addition, implanted monitors are less affected by environmental factors or influencing 'glucose-like' molecules which are not present in the body fluid (except mannose). There are already a few continuous-in-vivo glucose monitors commercially available, such as the devices offered by US-based companies Medtronic and Abbott. These sensors make use of subcutaneously implantable needle-type electrodes that measure glucose in the interstitial fluid using enzymatic reactions. The lifetimes of these needle-type implants is limited due to the instability of the enzymes used and have to be replaced after few days. Moreover, most needle-type implants still have a part of the read out internal (the needle) and part external (the electronics) and this bears the risk of causing infection and inflammation because of the openings through the dermis. Minimally invasive implants should be developed without external parts and with long implantation times.

SUMMARY OF THE INVENTION

In certain embodiments, the present invention provides a good method to (indirectly) determine the concentration of an analyte.

In certain embodiments, the present invention provides a device and a system suitable for performing such a method.

In certain embodiments, the present invention provides a use of such a device or such a system for measuring the glucose concentration in blood or in a blood sample.

Certain embodiments of the present invention are useful to (indirectly) determine a concentration of an analyte in a fluid or a fluid sample, e.g. in a blood sample.

In a first aspect, the present invention provides a method of determining or measuring the concentration of a predefined analyte in a fluid or fluid sample. The method comprises the steps of: a) providing a SERS substrate comprising predefined receptor molecules capable of binding predefined competitor molecules; b) contacting the SERS substrate with the fluid or fluid sample comprising said analyte in a concentration to be determined and comprising a predetermined concentration of said competitor molecules; c) radiating the SERS substrate with a monochromatic light source thereby generating a SERS signal having a level indicative of the amount of competitor molecules bound to the receptor molecules of the SERS substrate; d) determining the level of the SERS signal while radiating the SERS substrate with the monochromatic light source; and e) determining a concentration of the analyte in the fluid or fluid sample based on the level of the measured SERS signal.

It is an advantage of certain embodiments of the present invention that an improved technique is provided for (indirectly) determining the concentration of the analyte in a fluid, which technique is more sensitive than techniques known in the art.

It is an advantage of certain embodiments of the present invention that the concentration of the analyte in the fluid (sample) is determined by measuring the SERS signal of the competitor molecules when being radiated. The SERS signal is indirectly related to the concentration of analyte molecules present in the fluid (sample). This indirect measurement technique leads to an improved method and device with respect to sensitivity as the concentration of competitor molecules can be measured in a very sensitive manner. Thus, indirectly, the concentration of analyte molecules can be determined in a very sensitive manner. Also, the competitor molecules are specifically designed to give rise to a high SERS signal when being radiated.

In an embodiment, the method may be performed in vivo.

In an embodiment whereby the SERS substrate is pre-implanted, only the steps b) to e) are performed in vivo. Since the device is already implanted in the body, the method of determining the concentration does not require a surgical step.

It is an advantage of certain embodiments of the present invention to provide a method which can be performed at least partly subcutaneously and can last for a relatively long time in vivo, e.g. longer than four months, preferably longer than six months.

Alternatively the SERS substrate is not implanted in a human body, and all method steps may be performed completely outside of a human body. No surgery nor body penetration is required; the sole interaction with the human body in this case being for taking a blood sample, e.g. via insertion of a needle through the skin for taking a blood sample, e.g. by finger pricking.

Whether the method is performed in vivo or in vitro, it is an advantage of certain embodiments of the present invention that an improved technique for determining the concentration of an analyte in a fluid is performed, which technique is less invasive than techniques known in the art, as prior art techniques use blood sampling by pricking, to be done every day, while the substrate according to embodiments of the present invention only needs to be implanted once every six months.

It is an advantage of certain embodiments of the present invention to provide an improved technique for determining or measuring the concentration of the analyte in a liquid, which technique is more stable (e.g. with varying temperature) than techniques known in the art. In some embodiments, the disclosed technique can also be used if molecules other than the analyte are present in the sampled fluid.

It is an advantage of certain embodiments of the present invention that an improved technique is provided for determining or measuring the concentration of the analyte in a liquid, which is more reliable than techniques known in the art.

It is an advantage of certain embodiments of the present invention that a label-free technique is provided for determining or measuring the concentration of the analyte in a liquid, e.g. glucose concentration in a blood sample.

It is an advantage of certain embodiments of the present invention that a biocompatible technique is provided for determining or measuring the concentration of the analyte in a liquid, e.g. glucose concentration in a blood sample.

It is an advantage of certain embodiments of the present invention that a technique is provided for monitoring or measuring the concentration of an analyte in a fluid or one or more fluid samples in a time-continuous manner, whereby the concentration of the analyte can be detected or monitored or measured in real-time.

In certain particular embodiments, the receptor molecules are immobilized on the SERS substrate.

This enables an affinity reaction with the competitor molecule. It is an advantage that the receptor molecules enable affinity binding to competitor molecules. This enables a very sensitive technique for determining the concentration of the analyte in the fluid (sample) as the concentration of competitor molecules and the concentration of analyte are interrelated. If the concentration of competitor molecules detected at the surface is lower, the concentration of analyte molecules will be higher as the competitor molecules can bind to receptor molecules or to the analyte, but not to both at the same time.

In an embodiment, the receptor molecules are surface bound reversibly-binding diol-receptors for the competitor molecules.

As an advantage, diol-receptors can bind specific competitor molecules that give rise to a higher SERS signal when being radiated. The reversibly binding diol-receptors also allow a continuous monitoring. The diol-receptor molecule should be as small as possible, e.g. 2 nm or smaller, to allow for high signal enhancement of the competitor molecule within the active area of the SERS substrate. The chemical attachment of the diol-receptor to the SERS substrate should be stable e.g. via a covalent attachment scheme.

In an embodiment, the competitor molecules are molecules capable of binding either to the analyte molecules or to the receptor molecules.

As an advantage, the competitor molecules are in a continuous competition with the receptor and the analyte molecules. This competition leads to a continuous increase or decrease of the number of competitor molecules which are bound to the receptor molecules thereby allowing a continuous monitoring of the concentration of the analyte in a fluid (sample).

In an embodiment, the competitor molecules are boronic acid derivatives.

As an advantage, boronic acid derivatives give rise to a higher SERS signal compared to other types of competitor molecules.

In an embodiment, the boronic acid derivatives comprise a phenyl ring.

As an advantage, boronic acid derivatives comprising a phenyl ring generate a higher SERS signal when being radiated compared to boronic acid derivatives without a ring.

In an embodiment, determining (or measuring) the level of the SERS signal comprises determining (or measuring) the level of the SERS signal originating from the competitor molecules bound to the receptor molecules, using a Raman spectrometer.

In an embodiment, radiating the SERS substrate with a monochromatic light source comprises illuminating the SERS substrate through the dermis of skin tissue (e.g. through dermis of human skin) so as to generate surface enhanced Raman scattering light originating from the SERS substrate.

As an advantage, the method can be used with devices that are implanted under the skin of a patient.

In an embodiment, radiating the SERS substrate with a monochromatic light source comprises illuminating the SERS substrate through the dermis of skin tissue (e.g. through dermis of human skin) and illuminating both a sensing area and a reference area to generate surface enhanced Raman scattering light from the SERS substrate simultaneously and using the reference area for calibration of the sensor value.

It is an advantage of simultaneously illuminating the sensing area and a reference area having a known concentration of competitor molecules, in that the signal can be more easily calibrated. By illuminating both the sensing area and the reference area at the same time, the SERS signal from the reference area can be used to calibrate the SERS signal emanating from the sensing area. The SERS signal from the reference area can be used as a reference signal which may be correlated with the SERS signal from the sensing area to determine the concentration of the competitor molecules. Thereafter, the concentration of the analyte in the fluid or fluid sample may be determined using the determined concentration of the competitor molecules.

In an embodiment, the SERS substrate is a silicon-oxide substrate comprising metal nanostructures on the substrate surface.

As an advantage, the metal nanostructures give rise to a high SERS signal/response.

In an embodiment, the analyte is glucose.

According to a second aspect, the present invention provides a device for measuring the concentration of a predefined analyte in a fluid or fluid sample, the device comprising: a SERS substrate having a detection surface comprising receptor molecules for binding competitor molecules; a container atop the SERS substrate, the container comprising the competitor molecules, the competitor molecules being molecules capable of binding either to the predefined analyte molecules or to the receptor molecules; wherein the detection surface is encapsulated in a biocompatible package comprising a membrane configured to allow the analyte molecules to pass through and to prohibit the competitor molecules to pass through. The configuration may include selection of the size of the pores of the membrane which are adapted to the size of the analyte molecules. Pore size is selected such that analyte molecules may enter the container, but competitor molecules are trapped inside.

The device can be used to implement the method as described in the first aspect of the present invention. The container may be in contact with the surface comprising the receptor molecules. The container may be a gel, a cavity, a matrix, a fluid or any other substance or material which can contain receptor molecules.

It is an advantage that the detection surface is encapsulated in a biocompatible package. This allows implantation of the device in e.g. the human body. To determine the concentration of the analyte in the fluid (or fluid sample) by determining the amount of competitor molecules bound to the receptor molecules, the number of competitor molecules present in the container is fixed. It is an advantage that the membrane does not allow competitor molecules to pass through thereby keeping the number of the competitor molecules in the container constant.

As the membrane allows the passing through of analyte molecules and prevents the passing through of competitor molecules, it is an advantage that the device can be used to continuously monitor the concentration of analyte molecules based on the number of competitor molecules bound to receptor molecules (by measuring the SERS signal generated by the detection surface during the SERS measurement.

In an embodiment, the receptor molecules are diol molecules.

In an embodiment, the competitor molecules are boronic acid derivatives.

In an embodiment, the receptor molecules are immobilized on the SERS substrate.

In an embodiment, the receptor molecules are surface bound reversibly-binding diol receptors for the competitor molecules.

In an embodiment, the SERS substrate is a $SiO_2$ substrate comprising metal nanostructures on the substrate surface.

In an embodiment, the analyte molecules are glucose molecules.

Advantages of these device features are identical to the advantages of the corresponding features in the method embodiments.

According to a third aspect, the present invention provides a system for measuring the concentration of a predefined analyte in a fluid or fluid sample. The system comprises a device comprising a SERS substrate according to embodiments of the second aspect; a monochromatic light source for radiating the SERS substrate; a detector for determining the level of a SERS signal from the competitor molecules which are bound to the receptor molecules of the SERS substrate of the device; and a computational unit for determining a concentration of the analyte based on the level of the detected SERS signal.

In an embodiment, the competitor molecules are molecules which can bind either to the analyte molecules or to the receptor molecules.

In an embodiment, the competitor molecules are boronic acid derivatives.

In an embodiment, the boronic acid derivatives comprise a phenyl ring.

In an embodiment the detector comprises means for detecting the SERS signals of the competitor molecules bound to the receptor molecules with a Raman spectrometer.

In an embodiment, the monochromatic light source is configured for illuminating the SERS substrate through a dermis of skin tissue (e.g. through dermis of human skin) to generate surface enhanced Raman scattering light from the SERS substrate.

Advantages of the features of the system embodiments are identical to the advantages of the corresponding features in the method or device embodiments.

According to a fourth aspect, the present invention provides a use of a device according to the second aspect or a system according to the third aspect for measuring a concentration of glucose, in particular for measuring the concentration of glucose in blood or in a blood sample.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
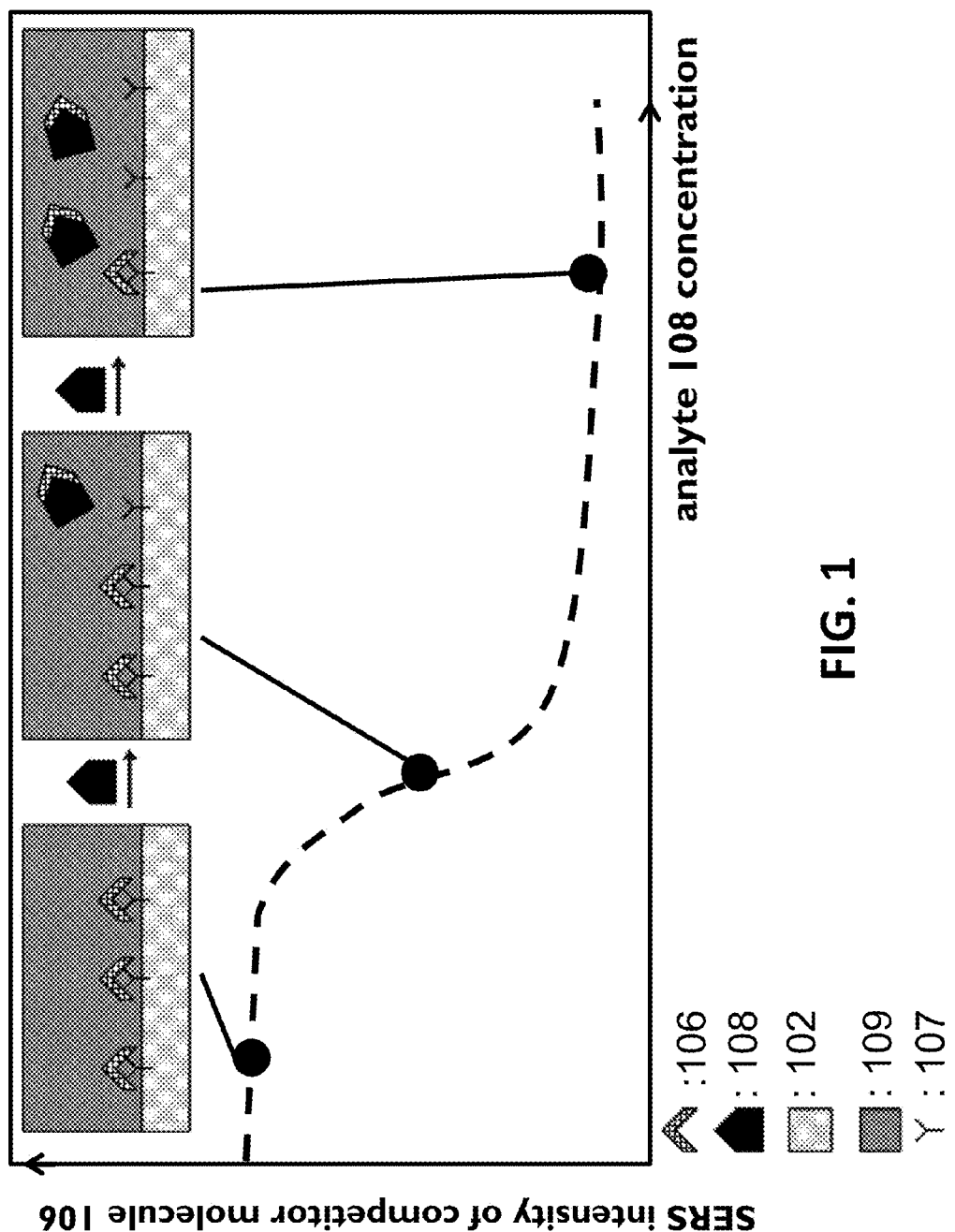
FIG. 1 illustrates the principle of detecting an analyte using an indirect assay technique according to an embodiment of the present invention.

The drawings are only schematic and are non-limiting. In the drawings, the size of some of the elements may be exaggerated and not drawn on scale for illustrative purposes.

Any reference signs in the claims shall not be construed as limiting the scope. In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

The terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from the present invention, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In the present invention, the notation "fluid (sample)" means "fluid or fluid sample". Likewise the notation "blood (sample)" means "blood or blood sample".

In the context of the present invention, an analyte is a substance or chemical constituent that is of interest in an analytical procedure.

In the context of the present invention, a receptor molecule is a molecule that occurs on the surface of a substrate, and that has a chemical and physical structure which helps it to interact freely with particular other molecules.

In the context of the present invention, a competitor molecule is a molecular species with competes between binding to an analyte and binding to a receptor molecule.

Figure 9:
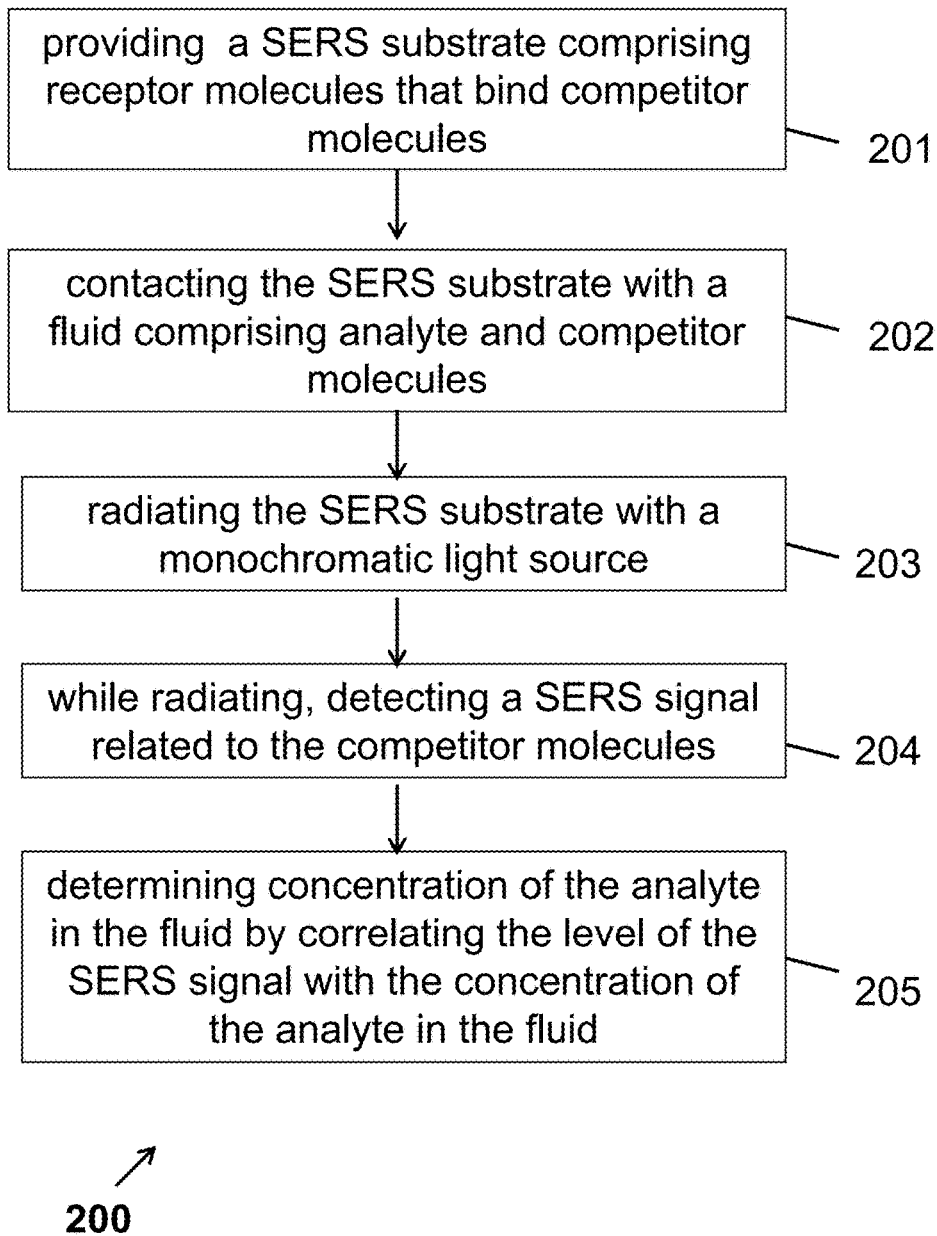
FIG. 9 is a flow chart of a method for determining a concentration of an analyte in a fluid, according to embodiments of the present invention.

FIG. 9 illustrates a method 200 according to embodiments of the present invention to measure the amount of analyte molecules 108 in a fluid (sample). The technique makes use of Surface Enhanced Raman Spectroscopy (SERS). SERS is a very sensitive technique able to measure small amounts of molecules, even at the single molecule level. It is a surface sensitive technique which results in the enhancement of Raman scattering by molecules adsorbed or bound (in close contact/in the vicinity of) on metal surfaces. Preferably these molecules are adsorbed on or bound to the metal surface.

A method of embodiments of the present invention makes use of an indirect assay method that measures the amount of competitor molecules 106 bound to receptor molecules 107 immobilized (immobilized being defined as "bound") on a SERS substrate surface 102 in order to measure the amount of analyte molecules 108 in a fluid (sample). The method as presented provides an improved way of detecting an analyte 108 in a solution whereby the method 200 is more stable than prior art techniques. The implementation of the method 200 comprises the use of a monochromatic light source 101, a modified SERS substrate 102 and a detector 103. A modified SERS substrate 102 is a SERS substrate on which surface chemistry has been applied for immobilizing receptor molecules 107 on the surface of the SERS substrate. The receptor molecules 107, immobilized on the substrate surface 102, are able to bind to competitor molecules 106.

Competitor molecules 106 are capable of selectively binding to the analyte molecule 108 and to the receptor molecule 107 (immobilized on the substrate), but cannot bind them simultaneously.

Figure 2:
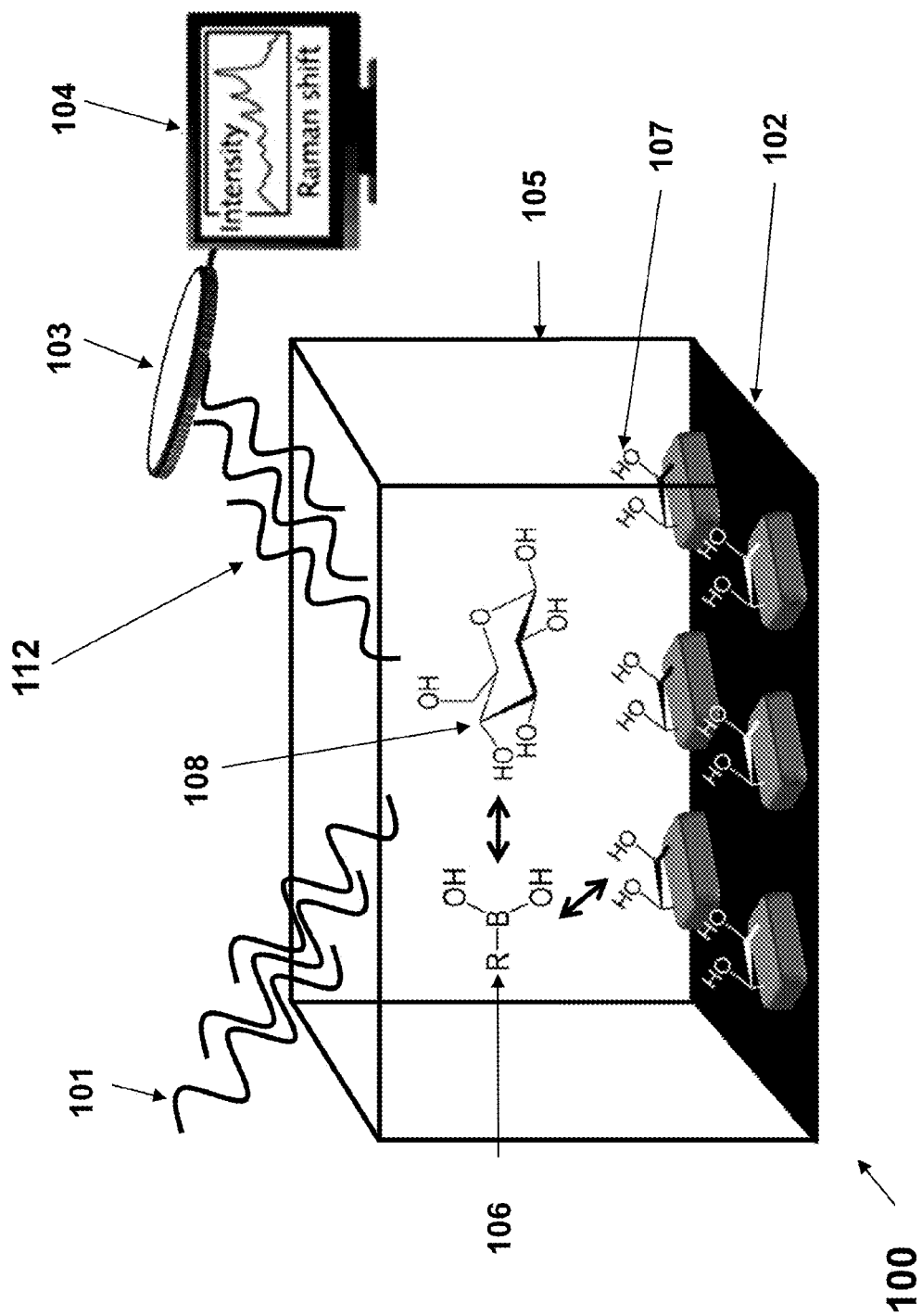
FIG. 2 illustrates a set-up for implementing the indirect competitive assay technique as can be used in embodiments of the present invention.

As illustrated also in FIG. 2, in order to detect the analyte 108, a fluid (sample) comprising competitor molecules 106 and analyte molecules 108 is provided onto the modified SERS substrate surface 102. The competitor molecules 106 are selected based on their binding properties to the receptor molecules 107 and to the analyte 108 in the liquid phase. The competitor molecules 106 can selectively bind to receptor molecules 107 and to analyte molecules 108. As such, when being provided on the SERS substrate surface, the competitor molecules 106 are in competition with the analyte molecules 108. A number of competitor molecules 106 will bind to the modified SERS substrate 102 surface, another number of competitor molecules 106 will bind to analyte molecules 108 in solution. In an equilibrium situation the number of competitor molecules 106 which are still bound to the SERS substrate surface 102 is related to the number of analyte molecules 108 in the fluid (sample).

Using the monochromatic light source 101, the modified SERS substrate 102, e.g. diol-modified SERS substrate, is radiated (illuminated). The amount of competitor molecules 106 which are bound to the modified SERS substrate surface 102 can be measured by recording with the Raman detector 103 the Raman scattered light 112 or (referred to as a "SERS signal" or "surface enhanced Raman scattering light") returning from the modified SERS substrate surface 102 during irradiation of this substrate 102. This gives rise to a SERS signal related to the presence of competitor molecules 106 on the modified SERS substrate surface 102. The amount of analyte molecules 108 is correlated to the number of competitor molecules 106 bound to the modified SERS substrate surface 102. The SERS signal is irreversibly related to the amount of analyte 108 present in the fluid (sample). The more analyte molecules 108 are present in the fluid (sample), the less competitor molecules 106 will bind to the modified SERS substrate surface 102; a lower SERS signal will be recorded, and vice versa as illustrated in FIG. 1. In addition, SERS is only sensitive to molecules which are in close proximity to the surface. Other matrix proteins which can be present in the analyte sample will not affect the detection. This is an advantage.

The presented technique is e.g. suitable for measuring glucose concentrations in the human body or in a human blood sample. The modified SERS substrate 102 with the competitor molecules 106 e.g. contained in a container 109 which is present on top of the modified SERS substrate 102, can be implanted in the human body. The monochromatic light source 101 and the detector 103 are external to the body. The monochromatic light source 101 (e.g. a laser) is capable of reaching the modified SERS substrate 102 through skin and the detector 103 is capable of recording a SERS signal 112 from molecules in close proximity to the modified SERS substrate 102 through the skin. It is pointed out that the laser light is merely used for providing a monochromatic light source for illumination and scattering purposes. The parameters of the laser light are selected such that the use of the laser light is completely harmless for human tissue, and does not treat nor cure a human being, and is not damaging to cells or tissue.

FIG. 1 illustrates a method 200 according to embodiments of the present invention. In the first stage (left part of the graph) a SERS substrate with receptor molecules 107 immobilized on the surface 102 is provided. On top of the SERS substrate 102 a fluid (sample) (e.g. a container 109) is present. The fluid (sample) comprises competitor molecules 106 capable of binding to the receptor molecules 107. The competitor molecules 106 give rise to a SERS signal when being radiated. In a second stage (middle part of the graph), analyte molecules 108 are added to the fluid (sample). A number of competitor molecules 106 will bind to the analyte molecules 108, giving rise to a lower SERS signal when being radiated. In a third stage (right part of the graph), more analyte molecules 108 are added to the fluid (sample) and they bind to more competitor molecules 106 resulting in a SERS signal which is lower. At a certain stage (far right part of the graph) the fluid (sample) is saturated with analyte molecules 108.

The measuring of the SERS signal is thus directly related to the number of analyte molecules 108 present in the fluid (sample). By selecting appropriate competitor molecules 106 which give rise to a high SERS signal when being radiated, the determination of the concentration of the analyte 108 in a fluid (sample) can be done more sensitive.

According to an embodiment of the invention, the competitor molecule 106 selection is done based on their affinity response for the analyte molecule 108 at physiological pH(7) whilst still generating a high SERS signal.

In order to sensitively detect glucose, a suitable surface chemistry for the SERS substrate (receptor molecule 107) needs to be selected. According to an embodiment of the invention, thiol-ed glucose is bound to the substrate. Any diol-molecule having an affinity for the SERS substrate can be used. The smaller the competitor molecule the better, since the SERS signal is strongly dependent on the distance between event and the substrate. In an embodiment, this distance is a few nanometers, typically 5 nanometer or less.

Figure 3A:
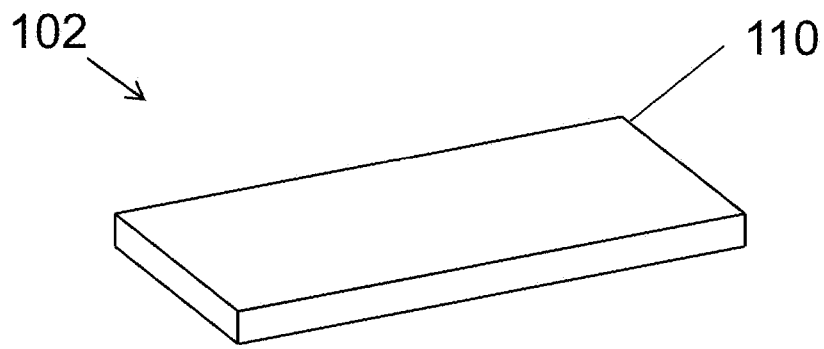
FIG. 3(a) illustrates a substrate as can be used in embodiments of the present invention.
Figure 3B:
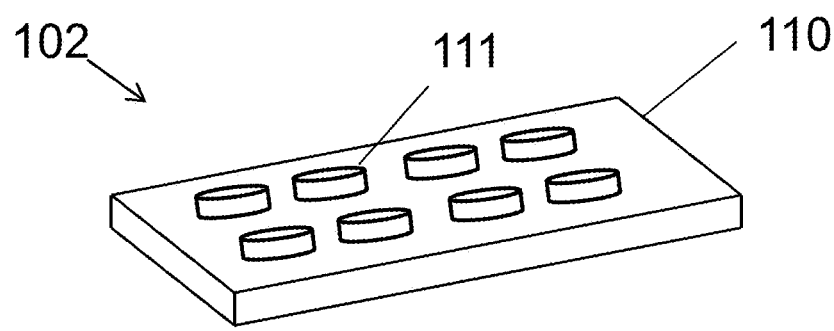
FIG. 3(b) illustrates a substrate with patterned nanostructures on its surface as can be used in embodiments of the present invention.
Figure 3C:
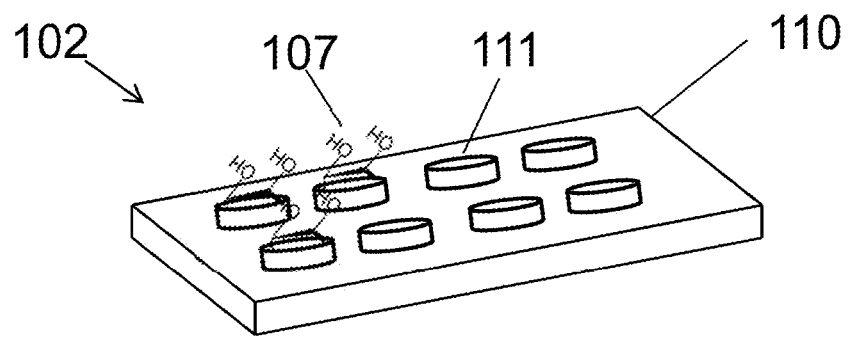
FIG. 3(c) illustrates a diol-modified substrate with patterned nanostructures on its surface as can be used in embodiments of the present invention.

FIGS. 3(a)-3(c) illustrate the process of fabricating a modified SERS substrate 102. FIG. 3(a) illustrates a substrate, e.g. a carrier substrate comprising a siliconoxide surface 110 (e.g. siliconoide). FIG. 3(b) illustrates metal nanostructures 111 which are patterned on the substrate. FIG. 3(c) illustrates a diol-modified SERS substrate 102 wherein diol molecules 107 are present on the metal nanostructures 111 of the substrate 102.

In an embodiment, the analyte 108 is glucose.

In an embodiment, the competitor molecules 106 are boronic acid molecules.

The competitor molecule 106 may be designed to have a large Raman cross section and to be capable of binding to either of the receptor molecule 107 and the analyte 108 with engineered affinity ratios at physiological pH (7).

Figure 4:
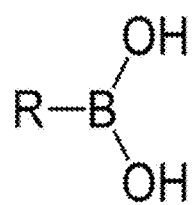
FIG. 4 illustrates a general boronic acid derivative where "R" can be different functionalities, as can be used in embodiments of the present invention.

In an embodiment the boronic acid molecules are boronic acid derivatives, as for instance illustrated in FIG. 4. Boronic acid derivatives are known to have affinity for disaccharides and can as such serve as an ideal competitor molecule in an indirect competitive assay. The boronic acid derivative gives rise to a SERS signal when being radiated. This is also a selection criterion for selecting a competitor molecule 106: a competitor molecule 106 is able to bind to receptor molecules, to analyte molecules 108 and to give rise to a SERS signal when being radiated.

In an embodiment, the receptor molecules 107 are diol molecules. In an embodiment, boronic acid derivatives 106 bind to diol molecules (receptor molecules 107) immobilized on the SERS substrate surface 102 or to glucose molecules 108. In an embodiment, a boronic acid molecule 106 is chosen from, but not limited to, the list of PBA, 4FFPBA, 3APBA, 5FMPBA, 3TBA as illustrated in FIGS. 6(a)-6(e).

In an embodiment, the boronic acid derivatives used as competitor molecules 106 feature a phenyl ring in its structure. Boronic acid derivatives comprising a phenyl ring can be greatly enhanced by SERS. When binding of the boronic acid derivative comprising a phenyl ring to the receptor molecules 107 immobilized on the SERS substrate occurs, this will give rise to a very high SERS signal when being radiated.

In an embodiment, boronic acid derivatives comprising a large scattering cross section are selected.

In an embodiment, the monochromatic light source 101 is a laser. In a particular embodiment, the monochromatic light source is an infrared or near-infrared light source. The monochromatic light source 101 can be a continuous or a pulsed monochromatic light source. In an embodiment, the monochromatic light source is a light source capable of penetrating tissue such as e.g. penetrating through the dermis of human skin, without damaging it, and without any therapeutic effect. In a particular embodiment the wavelength of the monochromatic light source is between 500 nm and 900 nm, for instance 532 nm, 633 nm or 785 nm. The wavelength of the monochromatic light of the radiation source may be selected based on its ability to penetrate through human skin. The monochromatic light source 101 can be any light source able to radiate the modified SERS substrate 102 through skin; the light generated by the light source having a wavelength which allows penetration through skin and its power as low as possible while still being sufficient to excite competitor molecules bound to the receptor molecules on the substrate surface measure a SERS signal. According to a specific embodiment the power of the monochromatic light source is suitable for medical applications, for instance not more than a few tens of mW, e.g. 1.2 mW in a focused mode.

In an embodiment, the radiating of the substrate 102 is done subsequently on different positions of the modified SERS substrate 102. For example, a ray of light from the light source illuminates different positions of the modified SERS substrate 102 thereby allowing continuous monitoring of the analyte 108 concentration in a fluid (sample).

In to an embodiment, the attachment of competitor molecules 106 to the surface of the SERS substrate 102 is enabled by the presence of receptor molecules 107 immobilized on the substrate surface. The receptor molecules 107 are immobilized on the SERS substrate to enable an affinity reaction with the competitor molecule 106. The receptors 107 are reversibly binding molecules allowing competitor molecules 106 to bound to and to be removed from the receptor molecule 107 when the competitor molecule binds to a analyte molecule. In an embodiment, the SERS substrate is a diol-modified SERS substrate 102.

In an embodiment, the SERS substrate comprises nanostructures 111. In an embodiment, the modified SERS substrate 102 comprises metal nanostructures. In an embodiment, the modified SERS substrate 102 comprises patterned metal nanostructures on the substrate surface. Nanostructures present on the surface of the substrate enhance the Raman scattering of molecules adsorbed on or in close vicinity of the surface. In a particular embodiment, the substrate is a silicon substrate, optionally covered with a silicon oxide layer on a surface. In a particular embodiment, the nanostructures are gold (Au), silver (Si) or copper (Cu) nanostructures or any other metal structure which enables Raman scattering enhancement. In an embodiment, atop the modified SERS substrate 102, a container 109 comprising competitor molecules 106 is present. The modified SERS substrate 102 and container 109 may be encapsulated in a biocompatible package if implantation in e.g. the human body is foreseen. Within the biocompatible package a predetermined number of competitor molecules 106 are present in the container 109. The competitor molecules 106 can bind to the modified SERS substrate 102 or to analyte molecules 108 which penetrate through the biocompatible package.

In an embodiment, the biocompatible package comprises a membrane 105 (see also FIG. 2). The membrane allows transfer of the analyte 108 through the membrane, inside container 109. While the concentration of the competitor molecules 106 needs to be fixed (in order to determine the concentration of the analyte 108 in the fluid (sample)) the membrane does not allow transfer of competitor molecules 106 through it. As such, the competitor molecules 106 are confined inside the biocompatible package, inside container 109. The membrane and container 109 allow penetration of light in order to radiate competitor molecules 106 which are bound to the modified SERS substrate 102.

In an embodiment, the biocompatible package has a shape which allows easy transfer of the capsule into e.g. the human body, e.g. elliptical, the present invention, however, not being limited thereto. In advantageous embodiments, the biocompatible package has no sharp edges.

In an embodiment, the area of the biocompatible package is 1.0 mm$^2$ or smaller.

The biocompatible package may be introduced into the body via incision or via a specific tool that is arranged for inserting the package into the body. The shape of the biocompatible package may also be adapted in order to fit into specific insertion tools. Alternatively the package may also be used outside of a human body.

In an embodiment, the membrane is a membrane fabricated from cellulose or cellophane such as dialysis membranes as known in the art.

In an embodiment, the concentration of competitor molecules 106 in the fluid (sample) is pre-determined. The actual amount of competitor molecules is a trade-off. In the fluid phase, the amount of competitor molecules should not be too high because then all analyte molecules will bind in the fluid phase and no analyte molecules will bind on the substrate.

In an embodiment, the detector 103 is a Raman spectrometer capable of detecting or recording a SERS signal. In a particular embodiment, the detector 103 is a holographic dispersive gratings or a CCD multichannel detector.

In a second aspect of the invention, a device for detecting an analyte, or for measuring the concentration of a particular analyte in a fluid (sample), is presented. The device allows the method as described in the first aspect of the invention to be performed. The device comprises a modified SERS substrate 102 with a container 109 (e.g. a gel, a fluid (sample)) on top of the surface of the substrate 102, encapsulated in a biocompatible package. The biocompatible package allows the device to be implanted into e.g. a human body, but that is not absolutely necessary, and the device may also be used outside of the human body. Within the biocompatible package a predetermined number of competitor molecules 106 are present inside the container 109. The competitor molecules 106 can bind to the SERS substrate 102 described above, and also to analyte molecules 108 which penetrate through the biocompatible package.

In an embodiment, the container 109 is a gel, a cavity, a matrix, a fluid (sample) or any other substance or material which can contain receptor molecules 107.

In an embodiment, the modified SERS substrate 102 is a diol-modified SERS substrate. The diol-modified SERS substrate allows binding of competitor molecules 106. In an embodiment, the competitor molecules 106 are boronic acid derivatives. FIG. 3(c) illustrates a substrate comprising metal nanostructures 111, each metal nanostructures comprises at least one diol molecule.

In an embodiment, the modified substrate 102 comprises nanostructures. In an embodiment, the substrate 102 comprises patterned metal nanostructures on the substrate 102 surface. Nanostructures present on the surface enhance the Raman scattering by molecules adsorbed on the surface. In a particular embodiment, the substrate 102 is a silicium (e.g. SiO2) support. In a particular embodiment, the nanostructures are gold (Au), silver (Si) or copper (Cu) nanostructures. Any other metal capable of Raman scattering enhancement may also be used. The metal nanostructures may be shaped or designed in order to give rise to a higher SERS signal, for instance they may be pyramids, pillars, star-shaped, or they may have any other suitable shape with sharp edges.

In an embodiment, the biocompatible package comprises a membrane 105. The membrane 105 may be a part of the biocompatible package. The membrane allows transfer of the analyte 108 through the membrane into the container 109. While the concentration of the competitor molecules 106 needs to be fixed (in order to determine the concentration of the analyte 108 in the fluid (sample)) the membrane does not allow transfer of competitor molecules 106 through it. The membrane and container 109 allows light for radiating the competitor molecules 106 to penetrate through.

In an embodiment, the membrane is a membrane fabricated from cellulose or cellophane such as dialysis membranes as known in the art.

In an embodiment, the competitor molecules 106 are a boronic acid derivatives, the receptor molecules 107 are diol molecules and the analyte 108 is glucose. According to an embodiment, the diol molecules are SH-glucose molecules.

The biocompatible package may be introduced into the body via incision or via a specific tool that is arranged for insertion into the body. The shape of the biocompatible package may also be adapted in order to fit into specific insertion tools. The biocompatible package may have a shape which allows easy transfer of the capsule into e.g. the human body.

In an embodiment, the size of the biocompatible capsule is a few $mm^2$ such as e.g. 10 $mm^2$ or less, 5 $mm^2$ or less, 1 $mm^2$ or smaller than 1 $mm^2$.

In a third aspect of the invention, a system 100 for carrying out the method as described in any of the embodiments of the first aspect of the invention, using the device as described in any of the embodiments of the second aspect of the invention is presented. The system comprises a monochromatic light source 101 as described in the first aspect of the invention, a device as described in the second aspect of the invention and a detector 103 for measuring a SERS signal. Such system 100 is illustrated in FIG. 2.

In an embodiment, the detector 103 is a RAMAN spectrometer.

The monochromatic light source 101 is activated to radiate a specific location of the modified SERS substrate 102. The SERS signal (SERS data) related to the amount of competitor molecules 106 bound to the surface of the modified SERS substrate 102 can be monitored and recorded using the RAMAN spectrometer 103.

Additionally a computational unit 104 can be used to gather SERS data, e.g., when continuous monitoring of the SERS signal, and correlate this to the concentration of the analyte 108 in a fluid (sample); the correlation being determining from the SERS signal the concentration of the analyte in the fluid (sample). In an embodiment, the computational unit 104 comprises a processor for processing the SERS data. The transfer of SERS data from the detector to the computational unit 104 can be done wirelessly or via a cable.

In an embodiment, the computational unit 104 is integrated in the detector 103 wherein the detector 103 further comprises a display for reporting the concentration of analyte to the user.

In another embodiment, the monochromatic light source 101, computational unit 104 and detector 103 are integrated into a single embedded system 100 which allows users to measure the concentration of an analyte 108 such as glucose in their bloodstream. The system 100 radiates a biocompatible package comprising a modified SERS substrate 102 which may be implanted in the user's body, or may be used outside of the body. The system 100 gathers SERS data related to the concentration of competitor molecules 106 and correlates the SERS data to the concentration of glucose (the analyte 108) in the blood (sample). The system 100 may further comprise a display and an interface for reviewing and accessing the measured information.

Also the use of a device as described above or a system as described above for measuring a concentration of glucose, e.g. in a blood stream or a blood sample is contemplated in embodiments of the present invention.

EXPERIMENTAL RESULTS

A. Fabrication of the SERS Substrates

During the experiments, one type of gold nanostructured SERS substrates were applied. Hereto, a bare $SiO_2$ substrate was cleaned prior to the deposition of polystyrene beads with a diameter of 100 nm (obtained from Thermo Fisher Scientific). Due to electrostatic forces, the nanoparticles form a closed-packed layer on the SiO2 substrate. Then, the substrate was carefully rinsed with $H_2O$. Afterwards, a thin layer of Au (~50 nm) was deposited onto the polystyrene-coated $SiO_2$ substrate using sputter deposition. The as such obtained SERS substrates were cleaned with an aceton-$H_2O$ mixture and dried with a stream of $N_2$. Additionally, the samples were cleaned using $UV-O_3$ treatment for 15 min prior to the experiments.

B. Functionalizing the SERS Substrate with Receptor Molecules

The SERS substrates were immerged into a solution containing 1 mM thiolated glucose for 3 days at room temperature in the dark (i.e. 1-Thio-β-D-glucose sodium salt dihydrate obtained from Toronto Research Chemicals). Due to the presence of the thiol functionalities, the molecules chemosorb onto the gold features of the SERS substrate by self-assembly. The thiolated glucose serves as a receptor molecule which binds boronic acid derivatives reversibly. Prior to use, the diol-functionalized SERS substrates were emerged in a carbonate buffer solution (100 mM, pH 10).

C. Monitoring of the Interaction Between a Diol-Modified SERS Substrate and Boronic Acid Derivatives First a rough selection of boronic acid derivatives (displayed in FIGS. 6(a)-(e)) was made based on their affinity for glucose. Phenyl boronic acid was selected for the presented set of experiments. The boronic acid derivatives were obtained from either BoroChem or Sigma-Aldrich and were applied without any purification.

Figure 5:
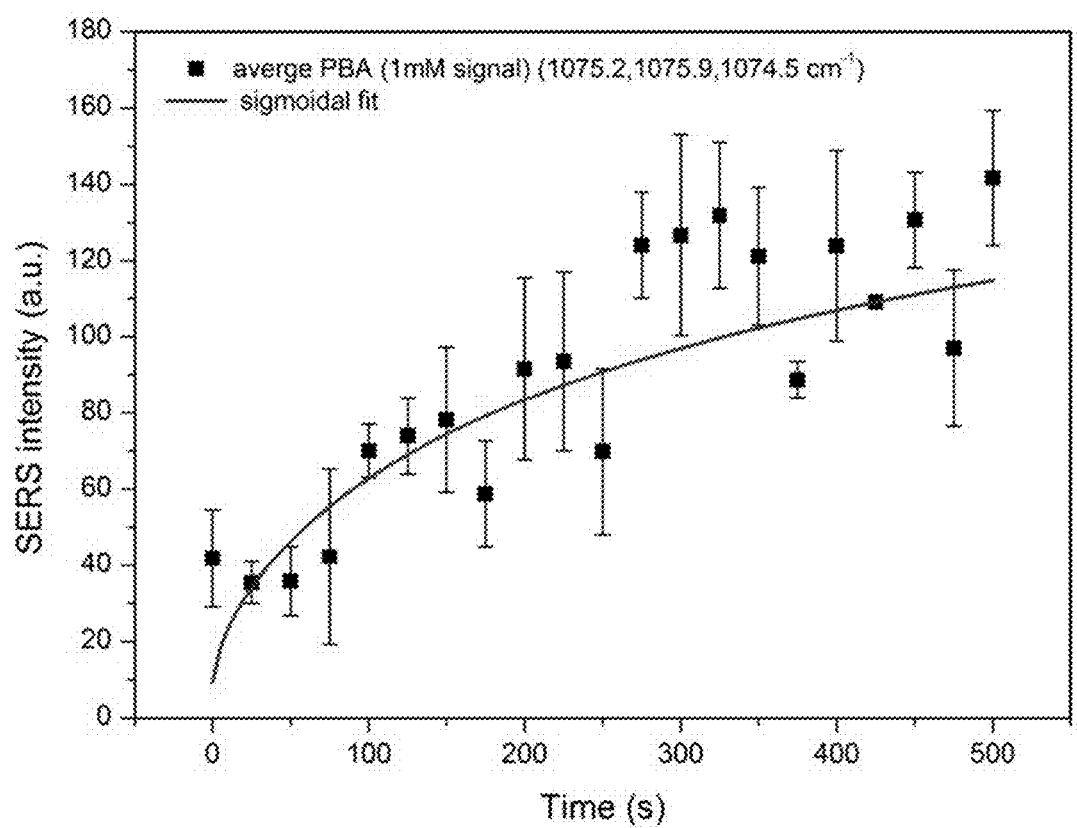
FIG. 5 illustrates the affinity of a competitor molecule (PBA) with receptor molecules (SHglucose) which are immobilized on a substrate with patterned nanostructures.
Figure 6A:
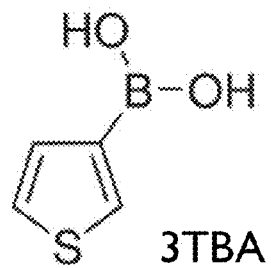
FIGS. 6(a) to 6(e) illustrate different boronic acid derivatives as can be used in embodiments of the present invention. The different BA derivatives all have a different affinity for glucose, while the molecules indicated with a '*' suffer from low solubility in $H_2O$ based solutions, for instance between 2 mM to 10 mM.
Figure 6B:
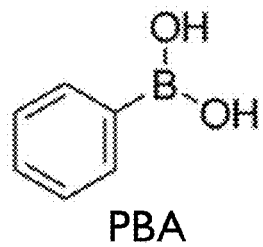
Figure 6C:
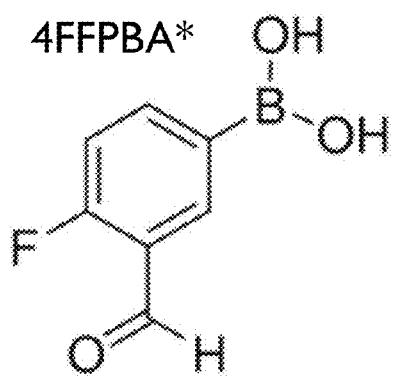
Figure 6D:
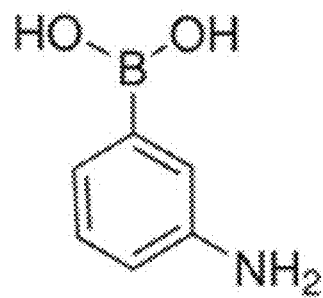
Figure 6E:
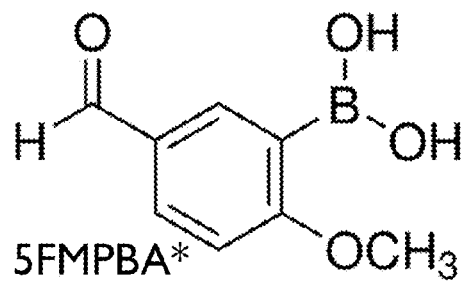
Figure 7:
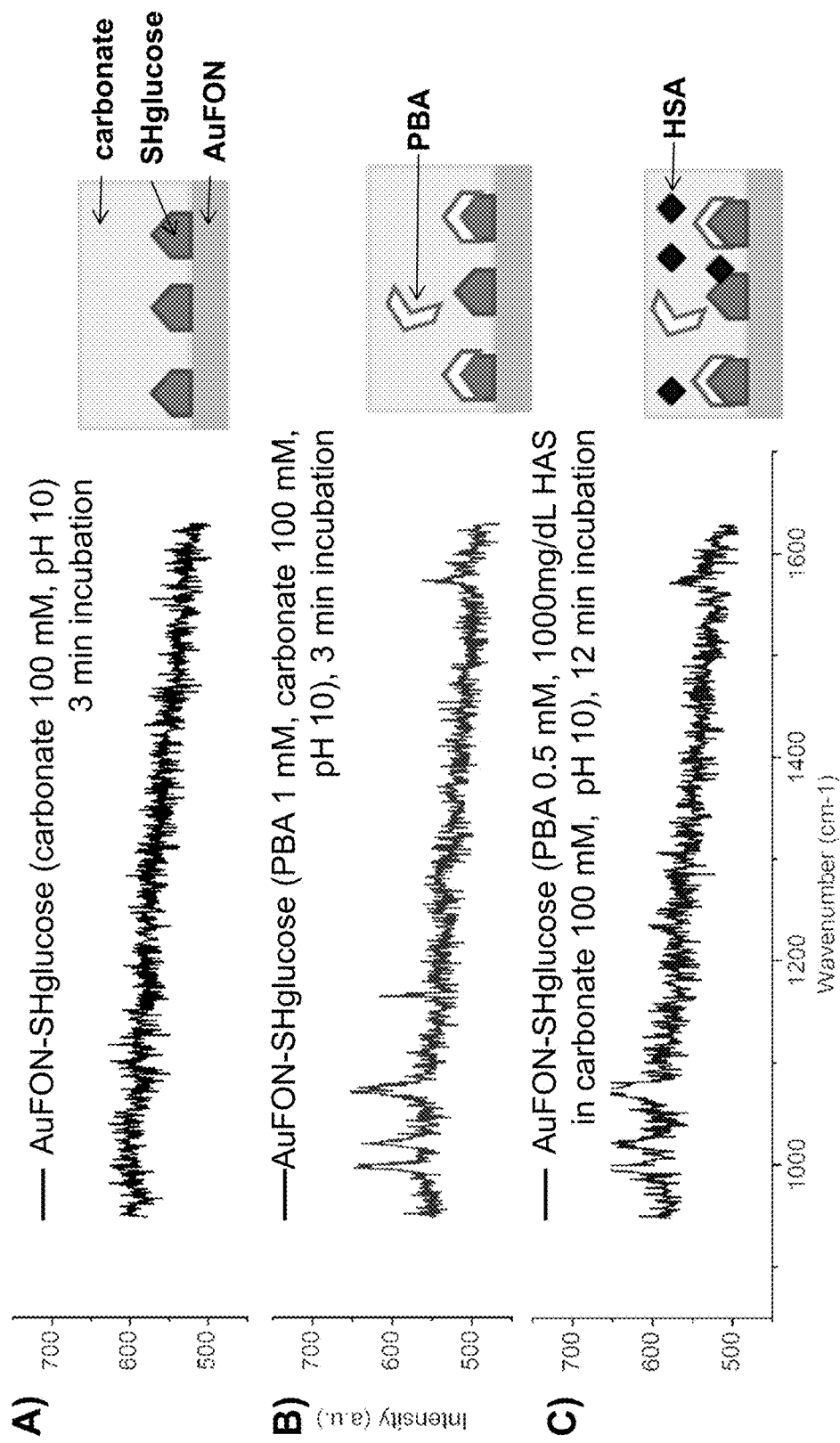
FIG. 7 illustrates the sensing of PBA in the presence of human serum albumin according to an embodiment of the present invention.
Figure 8:
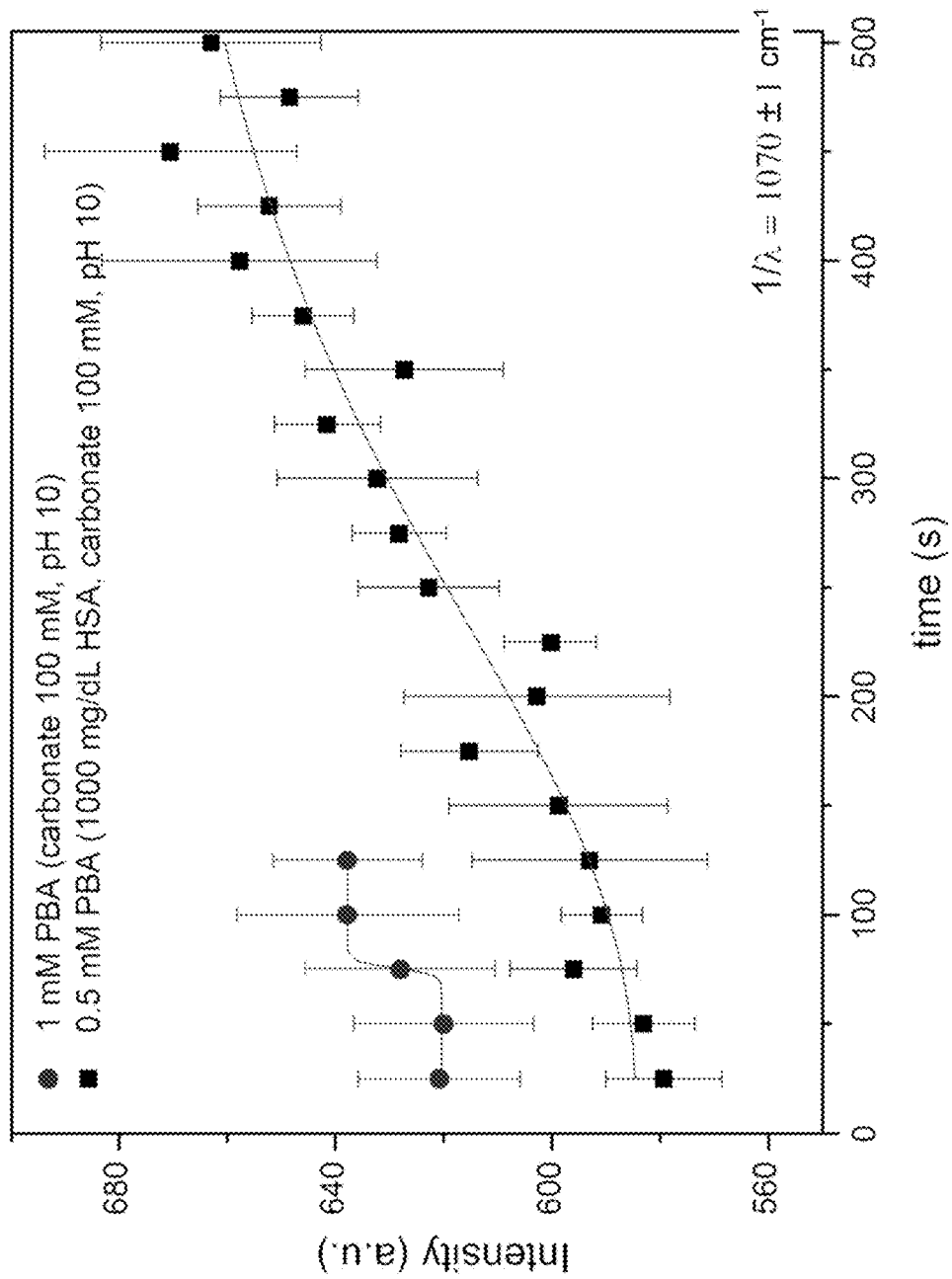
FIG. 8 illustrates kinetics of the binding between competitor molecule (PBA) and the receptor molecule (SHglucose) immobilized on a nano-patterned substrate.

The SERS substrates functionalized with the thiolated glucose molecules were mounted into a home-made flow cell connected to a peristaltic pump system. A continuous flow of carbonate buffer solution was applied (Part A) of FIG. 7). The corresponding Raman signal was monitored using a Raman setup of LabRAM. An integration time of 25 s and a 0.5 mW IR-laser (785 nm) was applied during the measurements. In FIG. 7 the raw SERS signals are plotted. In part A) of FIG. 7, no signal could be observed when applying the carbonate buffer solution. Then, a solution of 1 mM phenyl boronic acid (PBA) in carbonate was sent over the functionalized SERS substrate at a fixed flow rate generating a fingerprint spectrum as shown in part B) of FIG. 7. FIG. 5 represents the SERS intensity monitored at 1075±1 $cm^{-1}$ using a time interval of 25 s. Clearly, an increase of the signal is obtained over time, which is related the amount of PBA binding to the thiolated glucose moieties immobilized onto the SERS substrate. Similar studies were performed using different boronic acid derivatives showing less or more affinity for the immobilized glucose on the SERS substrate (data not shown). Furthermore, the same experiment was repeated, this time using a physiological background of matrix molecules (Part C) of FIG. 7). Hereto, human serum albumin (2000 mg/dl) was dissolved in carbonate solution and mixed in a 1/1 ratio with 1 mM PBA in carbonate. Despite the high background of matrix proteins, mimicking in vivo conditions, a clear SERS response of the PBA interacting with the immobilized thiolated glucose could be observed. The response was also measured in real time as represented in FIG. 8. The PBA is still able to interact with the immobilized glucose molecules (SHglucose) on the SERS substrate, even when applying a high background of matrix proteins (HAS). As such, the presented method is promising since it can be used in 'in vivo' conditions where there is always a high amount of proteins present.

Figure 10:
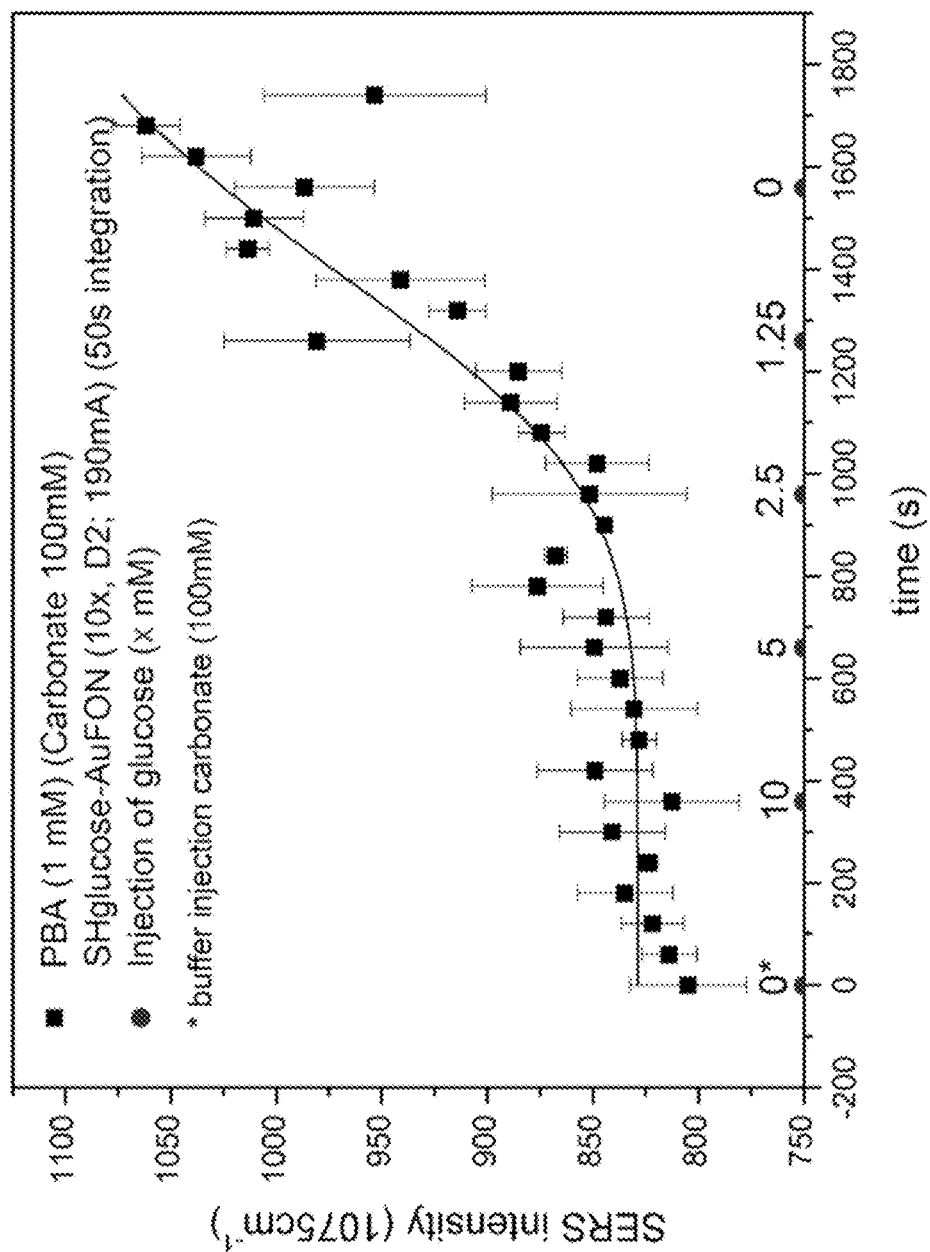
FIG. 10 illustrates an example of SERS signal intensity change over time while lowering the concentration of glucose.

D. Indirect Assay Using PBA as a Competitor Molecule for the Detection of Glucose Similar as to the experiments described above, a thiolated glucose functionalised SERS substrate was mounted into a home-build flow cell connected to a peristaltic pump. A 1/1 mixture of PBA (2 mM) with D-glucose (various concentration 20, 10, 5, 2.5 mM) was send sequentially over the SERS substrate. The SERS intensity at 1075±1 $cm^{-1}$ was monitored each 50s. In FIG. 10 a clear increase in the SERS signal was obtained after an injection of 2.5 mM glucose/1 mM PBA mixture. Lowering the concentration of glucose and maintaining the PBA concentration resulted in an increased SERS intensity. When there are less analyte (i.e. glucose) molecules present in the solution, the competitor molecule (PBA) is able to bind to the receptor molecules (immobilized glucose molecules) on the SERS substrate generating a SERS response. When the concentration of glucose molecules is too high (>2.5 mM), all the PBA molecules bind to the glucose molecules in the solution and no PBA molecules are available to bind with the immobilized glucose molecules on the SERS substrate. As such no SERS signal can be observed (similar as schematically represented in FIG. 1).

The human blood glucose levels fluctuate between 3 and 10 mM. The proposed indirect assay has to be sensitive particularly in this concentration range. To obtain a sensitive detection of glucose, other boronic acid derivatives can be applied which have a higher affinity for glucose. Also the concentration of competitor molecule can be optimized. If the concentration of boronic acid derivatives is too high, small concentration of glucose are difficult to distinguish. On the other hand, when the concentration of the boronic acid molecules is too low, high concentrations of glucose cannot be detected.

Figure 11:
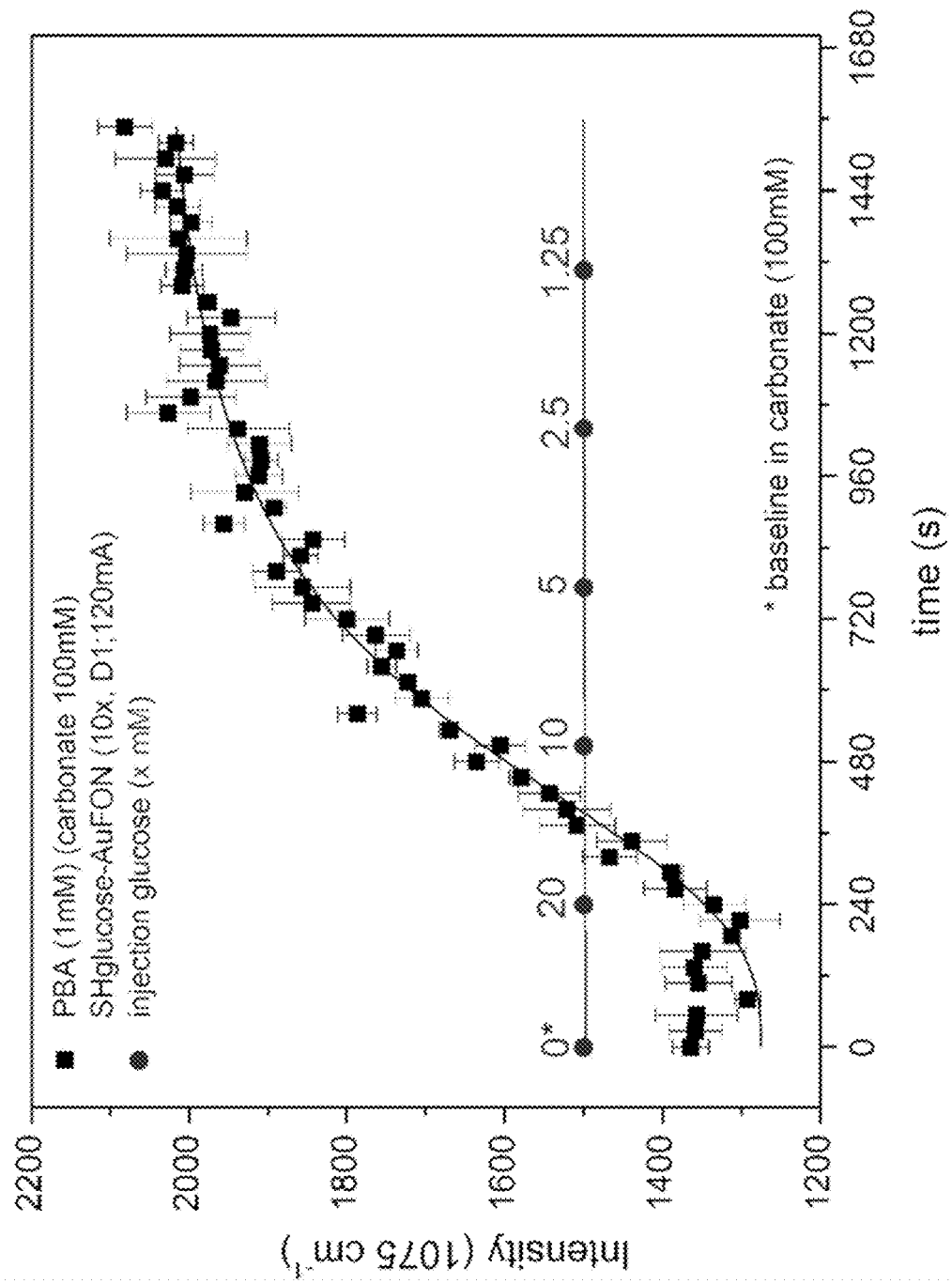
FIG. 11 illustrates another example of SERS signal intensity change over time while lowering the concentration of glucose.

Another method is to increase the reaction speed. Hereto we increased the applied laser power from 0.5 to 1.2 mW (illustrated in FIG. 11). By doing so, the SERS signal for the PBA molecule could be observed at 20 mM glucose and keeps increasing by lowering the glucose concentration.

The invention claimed is:

1. A method of determining the concentration of a predefined analyte in a fluid or fluid sample, the method comprising:
    a) providing a SERS substrate comprising a plurality of metal nanostructures and predefined receptor molecules capable of binding predefined competitor molecules, the receptor molecules being bound to the metal nanostructures, each of the competitor molecules being a molecule capable of reversibly binding to either of an analyte molecule and a receptor molecule, but being incapable of simultaneously binding both an analyte molecule and a receptor molecule;
    b) contacting the SERS substrate with the fluid or fluid sample comprising said analyte in a concentration to be determined and comprising a predetermined amount of said competitor molecules, such that the amount of competitor molecule bound to the receptor molecules at the metal nanostructures is an inverse function of the amount of analyte in the fluid or fluid sample, and such that when a competitor molecule is not bound to a receptor molecule, it is free to diffuse away from the metal nanostructures;
    c) radiating the SERS substrate with a monochromatic light source thereby generating a SERS signal having a level indicative of the amount of competitor molecules bound to the receptor molecules of the SERS substrate;
    d) determining the level of the SERS signal while radiating the SERS substrate with the monochromatic light source;
    e) determining a concentration of the analyte in the fluid or fluid sample based on the level of the measured SERS signal.

2. The method according to claim 1, wherein the receptor molecules are surface bound reversibly-binding diol-receptors for the competitor molecules.

3. The method according to claim 1, wherein the competitor molecules are boronic acid derivatives.

4. The method according to claim 3, wherein the competitor molecules are boronic acid derivatives comprising a phenyl ring.

5. The method according to claim 1, wherein measuring the level of the SERS signal comprises measuring the level of the SERS signal originating from the competitor molecules bound to the receptor molecules, using a Raman spectrometer.

6. The method according to claim 1, wherein radiating the SERS substrate with a monochromatic light source comprises illuminating the SERS substrate through the dermis of skin tissue so as to generate surface enhanced Raman scattering light originating from the SERS substrate.

7. The method according to claim 1, wherein the SERS substrate is a $SiO_2$ substrate comprising metal nanostructures on the substrate surface.

8. The method according to claim 1, wherein the SERS substrate is pre-implanted, and wherein the steps b) to e) are performed in vivo.

9. The method according to claim 1, wherein the analyte is glucose.

10. The method according to claim 1, wherein determining a concentration of the analyte in the fluid or fluid sample includes correlating the level of the measured SERS signal with the amount of competitor molecules.

11. The method according to claim 1, wherein a container is disposed atop the SERS substrate, the container comprising the competitor molecules, and wherein the SERS substrate is encapsulated in a biocompatible package comprising a membrane configured to allow the analyte molecules to pass through and to prohibit the competitor molecules to pass through.

12. The method according to claim 1, wherein the SERS substrate comprises metal nanostructures on the substrate surface.

13. The method according to claim 1, wherein
    the analyte is glucose;

the competitor molecules are boronic acid derivatives;
the receptor molecules are surface immobilized reversibly-binding diol-receptors capable of binding the competitor molecules.

14. The method according to claim 13, wherein the competitor molecules are boronic acid derivatives comprising a phenyl ring.

15. The method according to claim 14, wherein the SERS substrate comprises metal nanostructures on the substrate surface.

16. The method according to claim 14, wherein the diol-receptors are glucose moieites immobilized on the SERS substrate.

17. The method according to claim 14, wherein the diol-receptors are molecules 2 nm or smaller in size.

18. The method according to claim 14, wherein the diol-receptors are covalently bound to the metal nanostructures.

* * * * *